(12) United States Patent
Webb et al.

(10) Patent No.: US 9,375,136 B2
(45) Date of Patent: Jun. 28, 2016

(54) MULTI-FOCAL OPTICAL COMPONENT, OPTICAL SYSTEM, AND IMAGING METHOD

(75) Inventors: Watt W. Webb, Ithaca (IT); Chunhui (Chris) Xu, Ithaca, NY (US); Minghan Chen, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/574,340

(22) PCT Filed: Jan. 24, 2011

(86) PCT No.: PCT/US2011/022186
§ 371 (c)(1),
(2), (4) Date: Sep. 14, 2012

(87) PCT Pub. No.: WO2011/091340
PCT Pub. Date: Jul. 28, 2011

(65) Prior Publication Data
US 2013/0006056 A1    Jan. 3, 2013

Related U.S. Application Data

(60) Provisional application No. 61/297,551, filed on Jan. 22, 2010.

(51) Int. Cl.
*A61B 1/06* (2006.01)
*A61B 6/00* (2006.01)
(Continued)

(52) U.S. Cl.
CPC .............. *A61B 1/00188* (2013.01); *A61B 1/043* (2013.01); *A61B 5/0068* (2013.01); *A61B 5/0084* (2013.01); *G02B 3/10* (2013.01);
(Continued)

(58) Field of Classification Search
CPC .... G02B 3/10; G02B 21/0028; A61B 5/0068; A61B 1/00096
USPC .......... 359/385, 708–719; 600/160, 167, 172, 600/173, 178
See application file for complete search history.

(56) References Cited

U.S. PATENT DOCUMENTS 4,883,548 A * 11/1989 Onoki ............................. 156/99
4,952,040 A *  8/1990 Igarashi ....................... 359/708
(Continued)

OTHER PUBLICATIONS

Brewersdorf, Pick, Hell; Multifocal Multiphoton Microscopy, Optics Letters, vol. 23, No. 9, pp. 655-657, May 1, 1998.*

*Primary Examiner* — Matthew J Kasztejna
*Assistant Examiner* — Aaron B Fairchild
(74) *Attorney, Agent, or Firm* — William Greener; Bond, Schoeneck & King, PLLC (57) ABSTRACT

An optical lens comprising a lens body that transmits light in an optical path there through, wherein the lens body consists of an anterior surface, a posterior surface, and a medium there between, further wherein one of the anterior surface and the posterior surface has a single curvature and the other of the anterior surface and the posterior surface has at least two optical zones each having a different curvature. An optical system, comprising a multi-photon endoscope having a distal end, and the optical lens disposed in the distal end. A method for obtaining an image of an object comprising providing the multi-photon endoscope, propagating light from the endoscope scanner one optical zone of the lens to focus the light at a focus location, and propagating light from the scanner through a different optical zones of the lens to focus the light at a different focus location.

4 Claims, 12 Drawing Sheets

(51) Int. Cl.
  *G01J 3/42* (2006.01)
  *G02B 21/00* (2006.01)
  *G02B 21/06* (2006.01)
  *G02B 3/10* (2006.01)
  *A61B 1/00* (2006.01)
  *A61B 5/00* (2006.01)
  *A61B 1/04* (2006.01)
  *G02B 23/24* (2006.01)
(52) U.S. Cl.
  CPC ........ *G02B21/0028* (2013.01); *G02B 23/2423* (2013.01); *A61B 1/00172* (2013.01)

(56) References Cited

U.S. PATENT DOCUMENTS

| | | | |
|---|---|---|---|
| 5,446,565 A * | 8/1995 | Komma et al. | G02B 3/10 |
| 5,777,803 A * | 7/1998 | Ju et al. | 359/719 |
| 6,485,413 B1 | 11/2002 | Boppart et al. | |
| 6,940,610 B2 * | 9/2005 | Prinzhausen et al. | 356/609 |
| 7,616,986 B2 | 11/2009 | Seibel et al. | |
| 2001/0021069 A1 | 9/2001 | Kasai | |
| 2005/0140981 A1 | 6/2005 | Waelti | |

* cited by examiner

FIG. 11 excellent# MULTI-FOCAL OPTICAL COMPONENT, OPTICAL SYSTEM, AND IMAGING METHOD

CROSS-REFERENCE TO RELATED APPLICATIONS

This application claims priority to U.S. Provisional application Ser. No. 61/297,551 filed on Jan. 22, 2010, the subject matter of which is incorporated herein by reference in its entirety to the fullest allowable extent.

BACKGROUND OF THE INVENTION

1. Field of the Invention

Embodiments of the invention generally pertain to the field of optical imaging, more particularly to endoscopic apparatus/systems that can simultaneously acquire lower field of view (FOV), higher resolution images and wider FOV, lower resolution images and, most particularly to single, multi-focal optical components that enable simultaneous lower FOV, higher resolution imaging and wider FOV, lower resolution imaging, and use of such components in endoscopes and particularly multi-photon endoscopes (MPEs).

2. Description of Related Art

Multiphoton microscopy (MPM) is a powerful tool for biological imaging. It enables minimally invasive imaging of endogenous fluorescent species and harmonic generation, providing contrast in unstained tissues. By incorporating a miniaturized endoscope, medical multiphoton microscopic endoscopy (MPM-E) could play a significant role in, e.g., clinical cancer diagnosis. As presented in previous reports of multiphoton microscopic endoscopes (Jung & Schnitzer 2003; Wu et al 2009), MPM-E can facilitate noninvasive diagnosis of a diseased state in-situ, potentially becoming a valuable technology for clinical diagnosis.

A significant obstacle to the development of a practical MPM-E probe has been the need for optical zooming capability. During clinical diagnosis, low-magnification and large field of view (FOV) imaging would allow clinicians to survey a large area and locate the disease site and then perform high-resolution multiphoton imaging to confirm the diagnosis. For practical implementation, both the large FOV imaging and high-resolution imaging must be obtained with the same endoscope apparatus. While such an optical zooming capability is easily accomplished with conventional microscopes by using multiple objective lenses, achieving the same capability in a compact endoscope presents a significant challenge. Previous fiber based MPM-E designs (Jung & Schnitzer 2003; Wu et al. 2009; Fu et al. 2005; Le Harzic et al. 2008) utilized either monolithic components, such as gradient refractive index (GRIN) lenses, or compound lens assemblies. However, these endoscope probes do not provide optical zooming capability, although by scanning a small area using a galvo mirror or fiber scanner, magnified images could be obtained. This magnification, however, does not change optical resolution. Therefore, previous systems were limited to performing either high-resolution imaging with a small FOV or low-resolution imaging with a large FOV.

In view of the foregoing problems and disadvantages in the prior art, the inventors have recognized the need for a solution to these issues and the benefits and advantages, that could be realized by an optical component, a system incorporating said component (e.g., a multi-photon endoscope (MPE)), methods and applications of such apparatus and methods that would overcome the known shortcomings in the art.

SUMMARY

An embodiment of the invention is an optical lens. The lens includes a lens body that transmits light in an optical path there through, wherein the lens body consists of an anterior surface, a posterior surface, and a medium there between, further wherein either of the anterior surface or the posterior surface has a single curvature and the other has at least two optical zones each having a different curvature. According to various, non-limiting aspects: one of the at least two optical zones is in a central region of the surface; the curvature of the surface in the central region is concave and the curvature of the surface in the other optical zone is planar; the single curvature and the curvature of the surface in the central region have different magnitudes of curvature; the other of the anterior surface or the posterior surface has a third optical zone within the one optical zone in the central region of the surface; the curvature of the surface of one of the at least two optical zones is planar; the anterior surface has a single convex curvature and the posterior surface has a central concave curvature and a peripheral planar curvature, wherein the lens has two optical zones; the posterior surface has a second central concave curvature within the central concave curvature, wherein the lens has three optical zones; the anterior surface has a central planar curvature and a peripheral convex curvature and the posterior surface has a single convex curvature, wherein the lens has two optical zones; the anterior surface has a second peripheral convex curvature, wherein the lens has three optical zones.

An embodiment of the invention is an optical system. The optical system includes a lens having a lens body that transmits light in an optical path there through, wherein the lens body consists of an anterior surface, a posterior surface, and a medium there between, further wherein either of the anterior surface or the posterior surface has a single curvature and the other has at least two optical zones each having a different curvature, wherein the anterior surface has a single convex curvature and the posterior surface has a central concave curvature and a peripheral planar curvature, wherein the lens has two optical zones, and a secondary lens having first and second surfaces, disposed adjacent the central concave curvature, wherein neither of the first and second surfaces of the secondary lens extends past a plane containing the planar peripheral surface.

An embodiment of the invention is an optical system that includes a multi-photon endoscope having a distal end, and an optical lens disposed in the distal end, wherein the lens further includes a lens body that transmits light in an optical path there through, wherein the lens body consists of an anterior surface, a posterior surface, and a medium there between, further wherein one of the anterior surface and the posterior surface has a single curvature and the other of the anterior surface and the posterior surface has at least two optical zones each having a different curvature. In a non-limiting aspect, the optical lens is removably disposed in the distal end.

An embodiment of the invention is a method for obtaining an image of an object. The method includes providing a multi-photon endoscope including a scanner operably disposed therein and an optical lens disposed in a distal end of the endoscope, wherein the lens has a lens body that transmits light in an optical path there through, further wherein the lens body consists of an anterior surface, a posterior surface, and a medium there between, further wherein one of the anterior surface and the posterior surface has a single curvature and the other of the anterior surface and the posterior surface has at least two optical zones each having a different curvature; propagating light from the scanner through one of the at least two optical zones of the lens to focus the light at a focus location; and propagating light from the scanner through a different one of the at least two optical zones of the lens to focus the light at a different focus location. In a non-limiting aspect, the method further includes propagating light from the scanner through another different one of the at least two optical zones of the lens to focus the light at another different focus location. In a non-limiting aspect, propagating light from the scanner through one of the at least two optical zones of the lens to focus the light at a focus location comprises obtaining a higher resolution, lower field of view image of an object, and propagating light from the scanner through a different one of the at least two optical zones of the lens to focus the light at a different focus location comprises obtaining a lower resolution, larger field of view image of the object.

The foregoing and other objects, features, and advantages of embodiments of the present invention will be apparent from the following detailed description of the preferred embodiments, which make reference to the several drawing figures.

BRIEF DESCRIPTION OF THE DRAWINGS

FIG. 1 shows an optical lens according to an exemplary embodiment of the invention; a) a cross sectional profile view of a lens according to a non-limiting, exemplary aspect and, b) a schematic perspective view of the lens in (a);

FIG. 5($a$) schematically shows light rays traced through a bifocal lens assembly, according to an illustrative aspect of the invention; ($b$) shows a photo of a bifocal lens assembly in a lens holder where the center and peripheral optical zones are indicated by the image circular truncation of an underlying grid pattern;

FIG. 6 shows a schematic diagram of an exemplary embodiment of the MPE/lens system used in a multiphoton imaging aspect, capable of both wider FOV/lower resolution imaging and higher resolution/smaller FOV imaging; (a) Sample is placed at larger FOV/lower resolution imaging focal point; (b) Sample is placed at higher resolution/smaller FOV focal point;

FIGS. 10($a$), ($b$) show SHG, and (c), (d) show reflection images of a rat-tail tendon, acquired with (b, d) 0.50 NA and (a, c) 0.18 NA; the scale bars are 100 μm

DETAILED DESCRIPTION OF EXEMPLARY EMBODIMENT OF THE INVENTION

Reference will now be made in detail to the present exemplary embodiments of the invention, examples of which are illustrated in the accompanying drawings. Wherever possible, the same reference numbers will be used throughout the drawings to refer to the same or like parts.

An embodiment of the invention is directed to an optical lens having at least two optical zones over its surfaces such that input light can be focused at at least two locations along an optical axis of the lens.

Figure 1A:
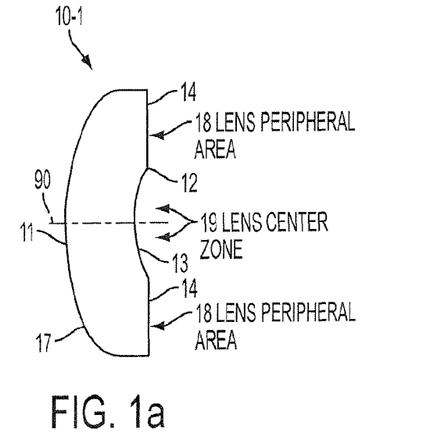
Figure 1B:
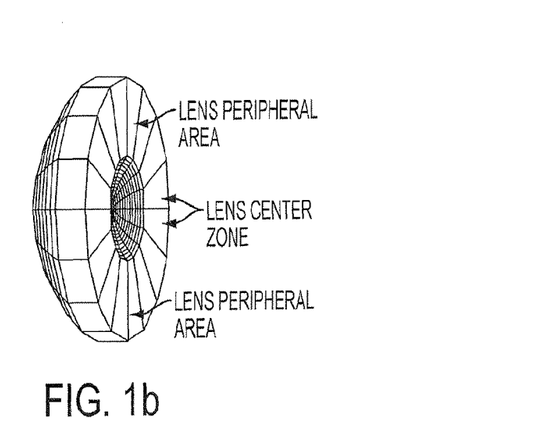

FIG. 1($a$) shows the cross sectional profile of an exemplary lens 10-1. The lens 10-1 has an anterior surface 11 and a posterior surface 12 (assuming input light from the left) and an optical axis 90 as shown. The anterior surface 11 has a single convex curvature 17 over its entire surface; however, the surface may be aspheric. The posterior surface 12 has a center region 19 having a concave curvature 13 and a peripheral region 18 having a planar curvature 14. The central region provides the lens with one optical zone for input light and the peripheral region provides the lens with another optical zone for input light. The magnitudes of the convex curvature 17 and the concave curvature 13 may or may not be equal depending on the design application. FIG. 1($b$) presents a perspective segment view of the lens 10-1.

Figure 2:
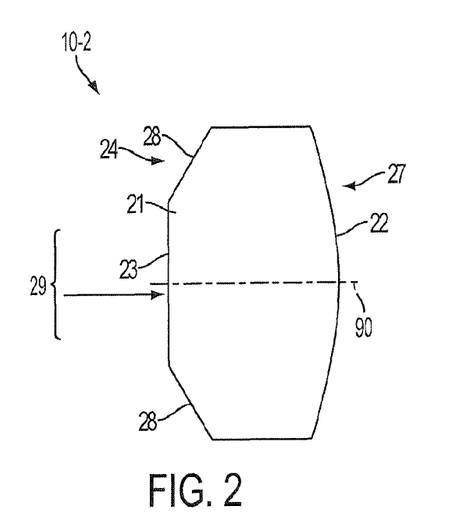
FIG. 2 shows a cross sectional profile view of a lens according to a non-limiting, exemplary aspect.

FIG. 2 shows a cross sectional profile of an alternative exemplary lens 10-2. Lens 10-2 has an anterior surface 21, a posterior surface 22 (assuming input light from the left) and an optical axis 90 as shown. The posterior surface 22 has a single convex curvature 27 over its entire surface; however, the surface may be aspheric. The anterior surface 21 has a center region 29 having a surface curvature 23 and a peripheral region 28 having a different curvature 24. The central region provides the lens with one optical zone for input light and the peripheral region provides the lens with another optical zone for input light. The magnitudes of the curvatures 23, 24, and 27 may or may not be equal depending on the design application.

Figure 3:
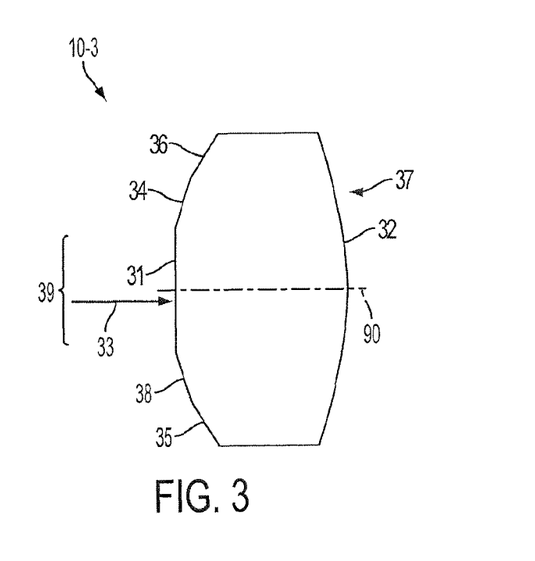
FIG. 3 shows a cross sectional profile view of a lens according to a non-limiting, exemplary aspect.

FIG. 3 shows a cross sectional profile of an alternative exemplary lens 10-3. Lens 10-3 has an anterior surface 31, a posterior surface 32 (assuming input light from the left) and an optical axis 90 as shown. The posterior surface 32 has a single convex curvature 37 over its entire surface; however, the surface may be aspheric. The anterior surface 31 has a center region 39 having a surface curvature 33, a first peripheral region 38 having a different curvature 34, and a second peripheral region 35 having a different curvature 36. The central region provides the lens with one optical zone for input light and the first and second peripheral regions provides the lens with two other optical zones for input light. The magnitudes of the curvatures may or may not be equal depending on the design application.

Figure 4:
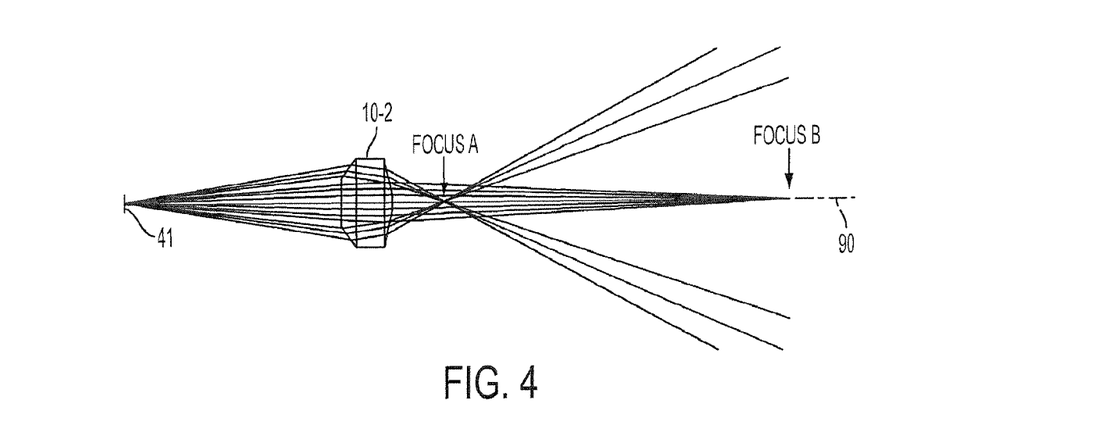
FIG. 4 shows a cross sectional profile view of the lens of FIG. 2 focusing input light at one position (Focus A) and at another focus position (Focus B), according to an illustrative aspect of the invention.

FIG. 4 schematically shows how the two optical zones of lens 10-2 simultaneously focus input light 41 at one respective focal position (Focus A) along the optical axis and at a second respective focal position (Focus B) along the optical axis, without the need to change the location of the lens along the optical axis.

Figure 5A:
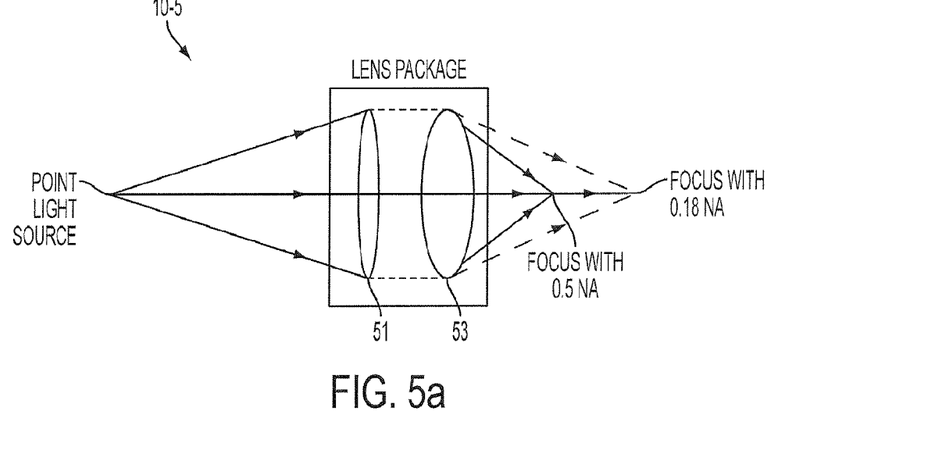
Figure 5B:
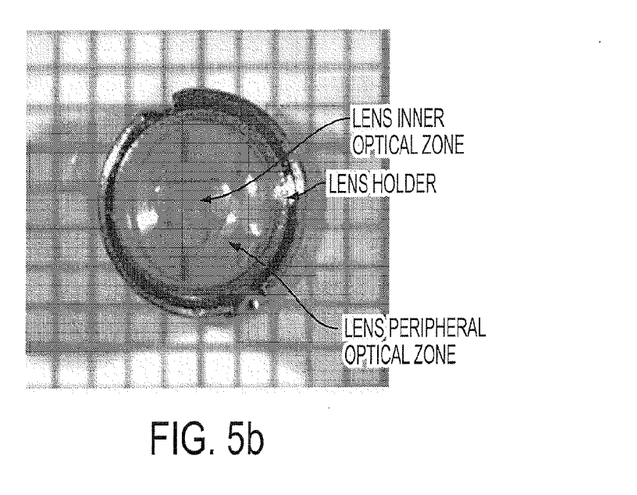

An exemplary lens assembly 10-5 was designed with Zemax software, and the ray-tracing diagram is schematically illustrated in FIG. 5($a$). Light emitting from a point source is focused by the lens assembly into two foci simultaneously with two different numerical apertures (NAs). The exemplary lens assembly includes a collimating lens 51 and a bifocal lens 53. The collimating lens was fabricated from a commercial lens (Edmund Optics NT46-342) by cutting down the peripheral areas of the lens so that a diameter of 4 mm is achieved. The bifocal lens was fabricated by first cutting an asphere lens (Edmund Optics NT-46343) into 4 mm diameter. Then, a center through-hole (5 mm length) was drilled, and a GRIN objective (GRINTECH GmbH) of 5 mm length was cemented into the through hole. The collimation lens and the focusing lens are in physical contact with each other. FIG. 5(b) shows the fabricated bifocal objective lens assembly. The lens outer diameter is 4.0 mm. The central optical zone is about 2 mm diameter, while the peripheral optical zone covers the remaining lens area. For a focal point with the 0.5 NA central zone, the Strehl ratios are 0.98, 0.50, and 0.25 at the center, 0.7, and full FOV (188 µm), respectively, which are typical of a GRIN objective. For a focal point with the 0.18 NA peripheral zone, the Strehl ratios are 0.89, 0.71 and 0.3 at the center, 0.7, and full FOV, respectively. At the peripheral area of the FOV, astigmatism and coma are the major aberrations. The bifocal lens assembly was fabricated using low-cost, commercially available lenses to demonstrate the feasibility of optical zooming. Off-axis aberrations can be significantly reduced by using customized lenses.

Using 800 nm center wavelength and assuming a 10 nm bandwidth, the calculated focal plane axial chromatic shifts are 1.4 and 8 µm for the 0.5 and 0.18 NA foci, respectively. Maximal lateral colors (lateral chromatic shift of the focus) at the image plane (at the largest FOV) are 0.006 and 0:02 µm for the 0.18 and 0.5 NA foci, respectively. These values are much smaller than the sizes of both foci. Furthermore, the values are significantly smaller than the pulse length in space (e.g., 30 µm for a 100 fs pulse). Thus chromatic aberration will not cause significant spatial and temporal distortion at the focus.

Another embodiment of the invention is directed to an optical system comprising a multi-photon endoscope (MPE).

Figure 6A:
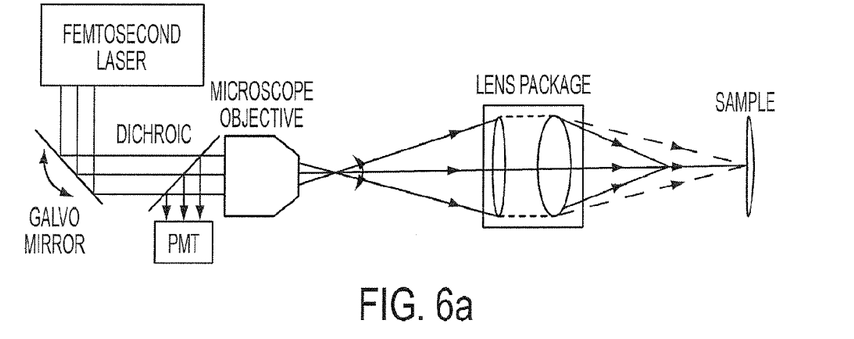
Figure 6B:
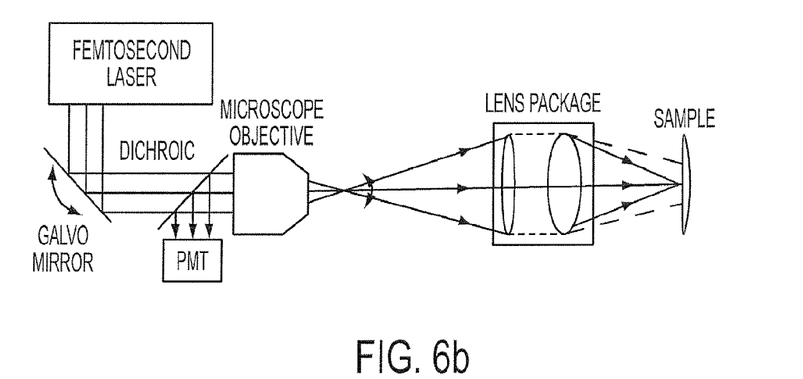

FIG. 6(a, b) show (in separation) an exemplary instrument setup for acquiring multiphoton (MF) images with a large FOV/low resolution and a small FOV/high resolution. Switching between the two imaging modes (a, b) does not require any optical or mechanical alteration of the imaging system, thus enabling a compact and convenient configuration for an MPE. By adjusting the relative distance between the endoscope assembly and the sample along the optical axis without lateral motion, the high-resolution image obtained was exactly at the center of the larger FOV image. In practice, lateral motion may need to be incorporated in the translation process to account for the possible motion of the object.

Figure 7A:
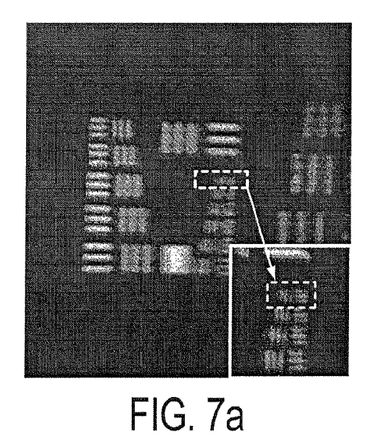
FIG. 7 shows reflection images (1 Hz frame rate) of a USAF target measured with NAs of (a) 0.18 and (b) 0.5; the insets in (a) and (b) are magnified images of the bars highlighted by the dotted line boxes.
Figure 7B:
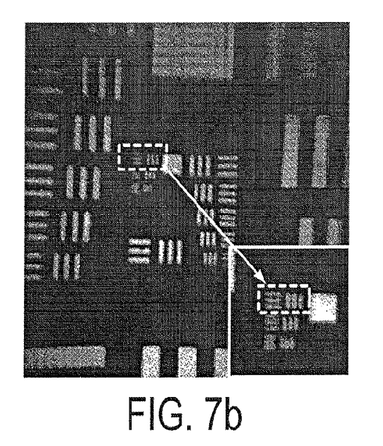

To characterize the lateral resolution, we examined the endoscope objective lens with a U.S. Air Force (USAF) target using one-photon reflection imaging. FIG. 7(a) shows the measured reflection image of a USAF target. To characterize the resolution limit of the lens, magnified images were obtained by scanning a small area in the center of the FOV. With a 0.18 NA, the simulated resolution is ~2:14 µm, which is close to the width of the group 7 element 6 (2.19 µm) [highlighted using the dashed rectangle in FIG. 7(a)]. Reflection images with the higher resolution (0.50 NA) were also measured with bars in groups 8 and 9 [FIG. 7(b)]. As indicated with the dashed rectangle in FIG. 7(b), the bar width of 0.977 µm can be resolved, which agrees very well with the theoretical resolution of 0.976 µm for a 0.5 NA optical system using 800 nm laser light.

Figure 8:
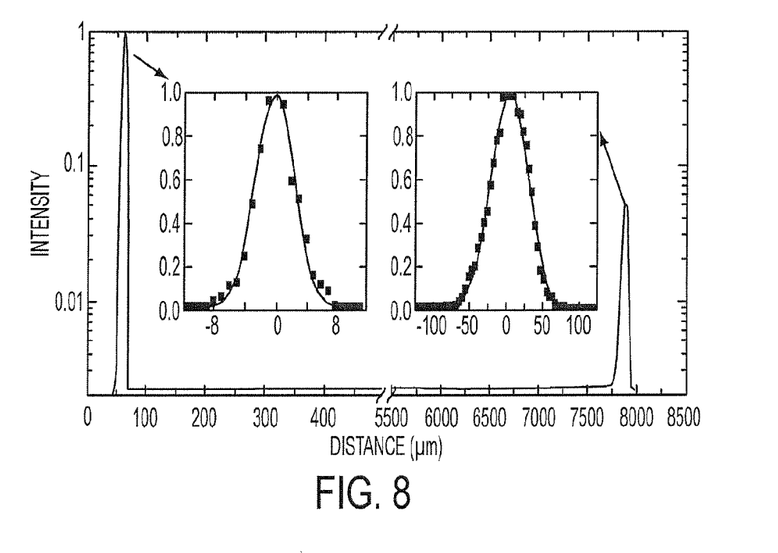
FIG. 8 shows fluorescence intensity axial profile (in logarithmic scale) of both foci through the center of a fluorescence bead along the axial direction. Normalized peak intensities with a solid line Gaussian fit are shown in inset figures.

Because the two foci of the bifocal lens are located coaxially along the optical axis, cross talk between the foci is a concern. The inherent axial sectioning capability of MPM (Denk et al. 1990) ensures that there is negligible out-of-focus background generation, removing the cross talk between the two imaging modes. Thus multiphoton imaging is naturally well suited for such a bifocal lens design. We characterized the lens axial resolution of the optical system by scanning through the center of 0.2 µm beads along the axial direction using a translation stage. As shown in FIG. 8, two foci were observed along the optical axis, with a separation of 7.8 mm. The fluorescence intensity of each focus was normalized and fitted with a Gaussian profile shown by the insets. The FWHM of the axial response for the 0.5 and 0.18 NA optical zones are 5.8 and 56 µm, respectively. The FWHM value of the 0.5 NA focus is close to the theoretical prediction of 4.63 µm. The small difference between the experiment and the theory is likely due to the chromatic aberration of the lens assembly. FIG. 8 clearly shows that the cross talk is negligible, and the presence of the second focus has negligible impact on multiphoton imaging. Similar to multiphoton imaging, a confocal pinhole can be added to reduce the cross talk of the two foci in single-photon magmg.

Figure 9A:
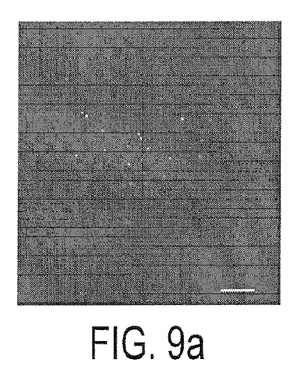
FIG. 9 shows multiphoton images of 6 μm beads fixed in agarose measured with 0.18 and 0.50 NA in (a) and (b), respectively; the horizontal scale bars are 100 μm.
Figure 9B:
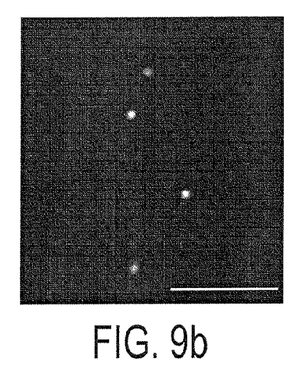

FIGS. 9(a) and 9(b) shows multiphoton images of 6 µm fluorescence beads fixed in agarose using the bifocal lens. In the lower resolution/wider FOV image, a large amount of beads were observed with an FOV of approximately 1 mm×1 mm, while the higher resolution image could identify the detailed features of individual beads clearly with a smaller FOV of 188 µm×188 µm.

Figure 10A:
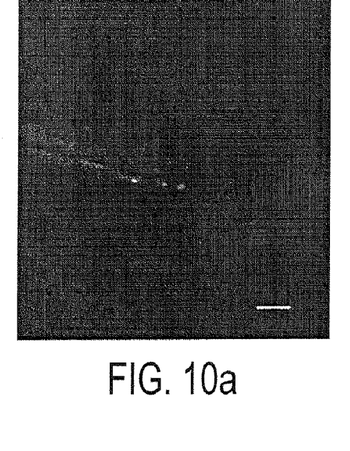
Figure 10B:
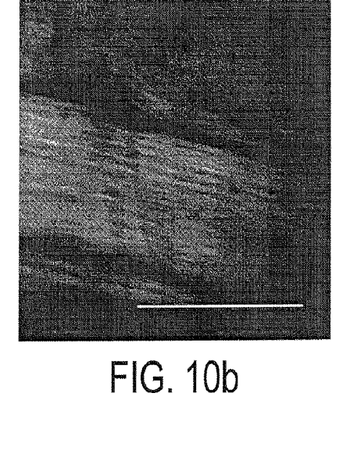
Figure 10C:
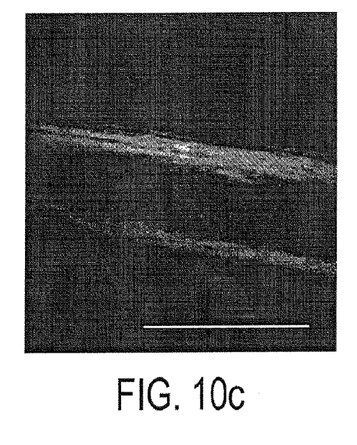
Figure 10D:
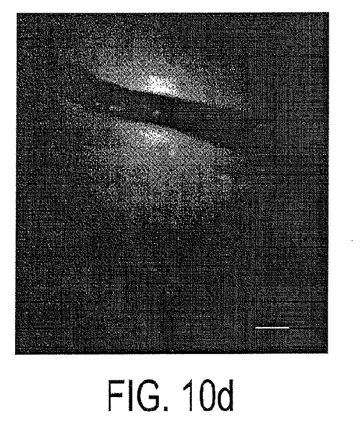

An average of 2 mW of laser power was focused at the sample, and both images were taken at a frame rate of 1 Hz. In addition to fluorescent beads, the second-harmonic generation (SHG) images of the collagen fibers of a rat-tail tendon were also obtained and are shown in FIGS. 10(a) and 10(b). The diameter of the entire collagen fiber is approximately 153 µm, as indicated in FIG. 10(a) using the low-NA peripheral imaging zone. After zooming in using the center high-NA optical zone, fine tendon structures are clearly resolved. The individual collagen fiber bundles are closely packed, with a diameter of approximately 1.3 µm for each bundle, which agrees very well with the value reported in the literature (Birk & Trelst 1986). About 4 and 13 mW of laser power were focused onto the rat-tail samples with the 0.5 and 0.18 NA, respectively. Because the laser beam is divided into two separate foci, compared with a conventional lens, a relatively higher laser power (approximately 1.5 times) was used with the bifocal lens. We also performed one photon reflection imaging of the rat-tail fibers, and the results are shown in FIGS. 10(c) and 10(d). Specular reflection, which is the reflection of light from the glass substrate, was observed in both images, which could be largely eliminated by using a confocal pinhole. SHG images show better contrast than that of reflection images with both NAs. Our experiments showed that a combination of one-photon reflected/scattered light imaging and multiphoton imaging can be achieved using the same lens. White light reflective/scattering approaches may also be useful for the far field view. Such a capability is valuable for clinical applications. For example, one-photon reflected light or confocal imaging may be preferred for the lower magnification/wider FOV survey, while multiphoton imaging may be optimum for higher resolution diagnosis. Further adjustment could be made for the FOVs and NAs in both optical zones in order to satisfy clinical application requirements.

Figure 11:
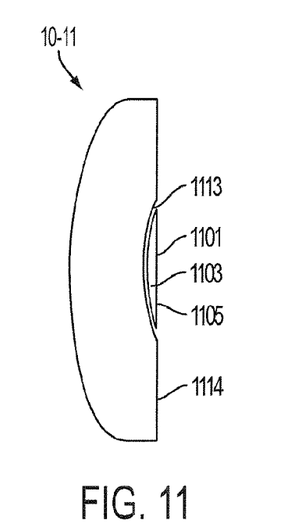
FIG. 11 shows an optical lens according to an alternative exemplary aspect of the invention.

FIG. 11 shows the cross sectional profile of an optical lens 10-11 according to a non-limiting exemplary aspect of the invention. The lens 10-11, as shown, is identical to lens 10-1 in FIG. 1 except that a secondary lens 1101 is disposed in the cavity in the central region of the primary lens. The secondary lens has an anterior surface 1103 having a convex curvature that may or may not be the same magnitude as the concave curvature 1113 of the primary lens, and a posterior surface 1105 that does not extend past the plane 1114 of the planar posterior surface of the primary lens.

Figure 12:
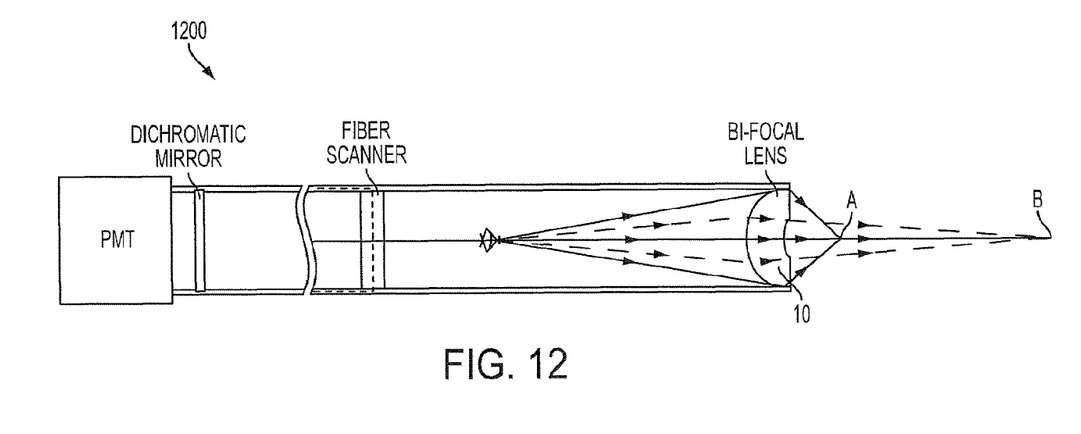
FIG. 12 shows in schematic cross section a multiphoton endoscope including a multi-focal lens, according to an exemplary embodiment of the invention.

FIG. 12 schematically shows the interior cross sectional profile of a non-limiting, exemplary multi-photon endoscope (MPE) 1200. A lens 10, such as any of the optical lenses described herein above, is disposed in the distal end of the endoscope. Target illumination light is delivered to the anterior surface of the lens 10 via the fiber scanner. The light propagating through the central region of the lens encounters a curved anterior surface and a curved posterior surface and is focused at point B, while the light propagating through the peripheral region of the lens encounters a curved anterior surface and a planar posterior surface (in the illustrated aspect) and is focused at point A. Point A represents lower resolution/wider FOV imaging of the target (not shown) and point B represents higher resolution/lower FOV imaging of the target.

The lens 10 may be incorporated in a module or otherwise disposed in the distal end of the MPE in a manner that it may be removed and replaced.

All references, including publications, patent applications, and patents cited herein are hereby incorporated by reference in their entireties to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. An optical system, comprising:
a multi-photon endoscope configured to enable multiphoton excitation fluorescence imaging having a distal end; and
a refractive optical lens configured to enable multiphoton excitation fluorescence imaging transmittance disposed in the distal end that can transmit visible light and multiphoton image-excitation light,
wherein the lens further comprises:
a focusing lens element consisting of a body of lens material having an anterior surface and a posterior surface, that transmits light in an optical path there through, and an optical axis,
wherein one of the anterior surface and the posterior surface has a single curvature and the other of the anterior surface and the posterior surface has at least two optical zones each having a different curvature,
further wherein the one of the at least two optical zones of the lens has a focus location along the optical axis; and the other one of the at least two optical zones of the lens has a different focus location along the optical axis.

2. The optical system of claim 1, wherein the optical lens is removeably disposed in the distal end.

3. A method for obtaining at least a multi-photon image of an object, comprising:
providing a multi-photon endoscope configured to enable multiphoton excitation fluorescence imaging including a scanner for delivering multi-photon imaging light operably disposed therein and a refractive optical lens configured to enable multiphoton excitation fluorescence imaging transmittance disposed in a distal end of the endoscope, wherein the lens comprises a lens element consisting of a body of lens material having an anterior surface and a posterior surface and an optical axis, that transmits light in an optical path there through, wherein one of the anterior surface and the posterior surface has a single curvature and the other of the anterior surface and the posterior surface has at least two optical zones each having a different curvature, further wherein the one of the at least two optical zones of the lens has a focus location along the optical axis; and the other one of the at least two optical zones of the lens has a different focus location along the optical axis;
propagating light from the scanner through one of the at least two optical zones of the lens to focus the light at the focus location and obtaining a higher resolution, lower field of view image of the object; and
propagating light from the scanner through a different one of the at least two optical zones of the lens to focus the light at the different focus location and obtaining a lower resolution, larger field of view image of the object.

4. The method of claim 3, further comprising propagating light from the scanner through another different one of the at least two optical zones of the lens to focus the light at another different focus location.

* * * * *